(12) United States Patent
Li et al.

(10) Patent No.: US 11,419,548 B2
(45) Date of Patent: Aug. 23, 2022

(54) FLEXIBLE PHOTONIC SKIN

(71) Applicant: TIANGONG UNIVERSITY, Tianjin (CN)

(72) Inventors: Hongqiang Li, Tianjin (CN); Rui Xie, Tianjin (CN); Xiaoqing Wei, Tianjin (CN); Jianing Wang, Tianjin (CN)

(73) Assignee: TIANGONG UNIVERSITY, Tianjin (CN)

( * ) Notice: Subject to any disclaimer, the term of this patent is extended or adjusted under 35 U.S.C. 154(b) by 252 days.

(21) Appl. No.: 16/829,953

(22) Filed: Mar. 25, 2020

(65) Prior Publication Data

US 2020/0359963 A1    Nov. 19, 2020

(30) Foreign Application Priority Data

May 14, 2019    (CN) .......................... 201910401403.X

(51) Int. Cl.
*A61B 5/0205*    (2006.01)
*A61B 5/00*    (2006.01)
(Continued)

(52) U.S. Cl.
CPC ........ *A61B 5/6832* (2013.01); *A61B 5/02055* (2013.01); *G02B 6/12004* (2013.01); *G02B 6/124* (2013.01); *G02B 6/12009* (2013.01); *A61B 5/021* (2013.01); *A61B 5/02438* (2013.01); *A61B 5/14532* (2013.01); *A61B 5/259* (2021.01); *A61B 5/282* (2021.01); *A61B 2562/228* (2013.01);
(Continued)

(58) Field of Classification Search
None
See application file for complete search history.

(56) References Cited

U.S. PATENT DOCUMENTS

2009/0312615 A1* 12/2009 Caduff ................. A61B 5/0531
600/347
2017/0164876 A1* 6/2017 Hyde .................... A61B 5/1118

OTHER PUBLICATIONS

Hongqiang Li et al. (2017). Chip-scale demonstration of hybrid III-V/silicon photonic integration for an FBG interrogator. Optica. 4. 692. 10.1364/OPTICA.4.000692 (Year: 2017).*

(Continued)

*Primary Examiner* — Nathan J Jenness
*Assistant Examiner* — James Moss
(74) *Attorney, Agent, or Firm* — Dragon Sun Law Firm, P.C.; Linggao Li, Esq.; Nathaniel Perkins

(57) ABSTRACT

A flexible photonic skin is provided, including a functional layer, an adhesive layer used for fixing the functional layer and made of hypoallergenic polyvinyl ethyl ether, and a packaging layer made of a polyurethane semi-transparent film and adhered to the adhesive layer, which are arranged successively from the top down, wherein the functional layer consists of two electrodes located on two sides and used for acquiring electrocardiographic signals of a human body, and a polymer-based photonic integrated chip located between the two electrodes and used for acquiring body temperature, pulse, blood pressure and blood glucose signals of the human body; and, the polymer-based photonic integrated chip processes and outputs the acquired electrocardiographic signals of the human body as well as the body temperature, pulse, blood pressure and blood glucose signals of the human body.

8 Claims, 3 Drawing Sheets

(51) Int. Cl.
  *G02B 6/12* (2006.01)
  *G02B 6/124* (2006.01)
  *A61B 5/021* (2006.01)
  *A61B 5/024* (2006.01)
  *A61B 5/145* (2006.01)
  *A61B 5/259* (2021.01)
  *A61B 5/282* (2021.01)

(52) U.S. Cl.
  CPC .............. *G02B 2006/12097* (2013.01); *G02B 2006/12107* (2013.01); *G02B 2006/12138* (2013.01); *G02B 2006/12142* (2013.01)

(56) References Cited

OTHER PUBLICATIONS

Thomas Ferrotti. Design, fabrication and characterization of a hybrid III-V on silicon transmitter for high-speed communications. Other. Université de Lyon, 2016. English. ffNNT : 2016LYSEC054ffffel-01529424f (Year: 2016).*

Jack Sheng Kee et al. "Design and fabrication of Poly(dimethylsiloxane) arrayed waveguide grating," Opt. Express 18, 21732-21742 (2010) (Year: 2010).*

* cited by examiner

FLEXIBLE PHOTONIC SKIN

CROSS-REFERENCE TO RELATED PATENT APPLICATION

This application claims priority to and the benefit of CN 201910401403X, filed May 14, 2019, entitled "FLEXIBLE PHOTONIC SKIN," by Hongqiang LI et al. The entire disclosure of the above-identified application is incorporated herein by reference.

Some references, which may include patents, patent applications, and various publications, are cited and discussed in the description of the present disclosure. The citation and/or discussion of such references is provided merely to clarify the description of the present disclosure and is not an admission that any such reference is "prior art" to the present disclosure described herein. All references cited and discussed in this specification are incorporated herein by reference in their entireties and to the same extent as if each reference was individually incorporated by reference.

TECHNICAL FIELD

The present invention relates to a human body information detection device, and in particular to a flexible photonic skin available for measuring physiological information such as body temperature, pulse, blood pressure, blood glucose and electrocardiogram of a human body.

BACKGROUND OF THE PRESENT INVENTION

For the past few years, various wearable applications have developed vigorously, and revolutionary wearable applications emerge one after another. As important constituents in wearable systems, wearable sensors with various functions can be used for measuring physical and chemical parameters related to various physiological information of the human body, such as body temperature, electromyogram, heart rate, blood glucose and the like, and can also be used for measuring various motion states of the human body, such as acceleration, muscle extension, foot pressure and the like. These wearable sensors can also measure parameters related to the ambient environment, such as position coordinates, ambient temperature, humidity, atmospheric pressure and the like. These wearable sensors with different functions and shapes provide important tools to solve sensing and measurement problems in fields such as health, medical treatment, sports, industry and military.

Due to the limitations of electronic technology and material science, early wearable devices are mainly large backpacks and waist packs, which are very inconvenient to wear and carry. B. Firoozbakhsh et al. fabricated a wearable smart shirt available for measuring electrocardiogram, heart rate, body temperature and respiration. T. Linz et al. designed a shirt available for detecting the heart rate by using a conductive yarn interconnection technology. P. Grossman et al. invented the LifeShirt to realize the measurement of electrocardiogram, heart rate, posture, activity, respiration, blood pressure, body temperature and blood oxygen saturation. D. Curone et al. invented a ProTEX garment which could measure the heart rate, respiration, body temperature and blood oxygen saturation. R. Paradiso et al. invented a WEALTHY system implanted into an integrated sensor, which could realize the monitoring of electrocardiogram, heart rate, respiration and activity. N. Noury et al. invented a VTAMN system which could measure the heart rate, respiration, body temperature and activity. W. B. Gu et al. invented an h-Shirt system which could measure the electrocardiogram, pulse, heart rate and blood pressure.

At present, flexible wearable electronic sensors have developed rapidly and can be used for detecting various physiological information of a human body, including respiration, body temperature, pulse and motion monitoring. The wearable electronic sensors convert, in a signal conduction manner, external stimulation signals into electrical signals or other forms that are easy to output. There are mainly three common sensing conversion modes, i.e., piezoresistive effect, capacitive effect and piezoelectric effect. With the latest application of flexible wearable electronic materials such as inorganic semiconductor, organic material and carbon material, sensing devices can be directly attached to the skin surface, so that a series of health information such as blood pressure, blood glucose and pulse can be acquired, and the information are collected in an intelligent device for analysis and extraction so as to help doctors in diagnosis. The electronic skin, which is a novel wearable flexible bionic tactile sensor, is an artificial flexible electronic device for realizing the function of imitating human tactile perception. D. H. Kim et al. invented a multifunctional skin electronic device for monitoring electrophysiology, body temperature and strain. G. Schwartz et al. invented a flexible capacitive pressure sensor for measuring the pressure pulse of radial artery. T. Someya invented an e-skin integrated with pressure and body temperature sensors. T. Yamada et al. invented a bandage strain sensor for monitoring respiration. W. Jia et al. invented an electrochemical biosensor for real-time noninvasive lactic acid monitoring of sweat of a human body. Shen Guozhen of the Semiconductor Research Institute of Chinese Academy of Sciences and Professor Jiang Kai of the PLA General Hospital developed an ultra-thin and high-definition flexible electronic skin array which could be directly attached to the skin of a human body. The approaches to detect signals on the skin of the human body are more flexible, or even it is allowed to monitor physiological information in a place outside the hospital. The approaches to treat diseases, particularly health monitoring approaches, are gradually changed.

It can be found by analysis on the above documents that the development of most wearable sensors is based on electrical sensors up to now. These sensors measure the changes in electrical properties such as resistance, current and voltage of sensors. These sensors are susceptible to electromagnetic interference, complicated in structure, difficult in distributed sensing and the like.

Therefore, a heretofore unaddressed need exists in the art to address the aforementioned deficiencies and inadequacies.

SUMMARY OF THE PRESENT INVENTION

A technical problem to be solved by the present invention is to provide a flexible photonic skin which is flexible and wearable and used for measuring vital signs of a human body.

The present invention employs the following technical solutions. A flexible photonic skin is provided, including a functional layer, an adhesive layer used for fixing the functional layer which made of hypoallergenic polyvinyl ethyl ether, and a packaging layer made of a polyurethane semi-transparent film and adhered to the adhesive layer, which are arranged successively from the top down, wherein the functional layer consists of two electrodes located on two sides and used for acquiring electrocardiographic signals of a human body, and a polymer-based photonic integrated chip located between the two electrodes and used for acquiring body temperature, pulse, blood pressure and blood glucose signals of the human body; and, the polymer-based photonic integrated chip processes and outputs the acquired electrocardiographic signals of the human body as well as the body temperature, pulse, blood pressure and blood glucose signals of the human body.

The polymer-based photonic integrated chip includes a PDMS substrate; a Bragg waveguide grating array, an input grating coupler array arranged below a light source, a Multi-Mode Interference (MMI) coupler, an arrayed waveguide grating, an output grating coupler array and an MZI electrooptical modulator, which all are connected through optical waveguides, are arranged on the PDMS substrate, respectively; a photodetector array is arranged on the output grating coupler array; a light input and a light output of the Bragg waveguide grating array are connected to a first 2×2 coupler through optical waveguides; the input grating coupler array receives output light from the light source that is divided into two paths, with one path of light passing through a first 2×1 coupler to an input end of a second 2×1 coupler through the optical waveguides, and the other path of light passing through a second 2×2 coupler to be separately connected to the MZI electrooptical modulator and a light input end of the second 2×1 coupler through the optical waveguides; a light output end of the second 2×1 coupler is connected to a light input end of the MMI coupler; a light output end of the MMI coupler is connected to the Bragg waveguide grating array through the optical waveguides; and, the light output finally coupled by the MMI coupler passes through the arrayed waveguide grating and the output grating coupler array to the photodetector array for outputting by means of optical waveguide.

The first 2×2 coupler, the second 2×2 coupler, the first 2×1 coupler and the second 2×1 coupler are all MMI couplers.

The light source is bonded to the input grating coupler array through BCB polymer.

The photodetector array is bonded to the output grating coupler array through BCB polymer.

The MZI electrooptical modulator includes a first electrode, a ground and a second electrode which are arranged in parallel, wherein a first waveguide arm is arranged between the first electrode and the ground, and a second waveguide arm is arranged between the ground and the second electrode; input ends of the first waveguide arm and the second waveguide arm are connected to a coupled light source output from the second 2×2 coupler through the optical waveguides; output ends of the first waveguide arm and the second waveguide arm are connected to the input end of the output grating coupler array through the optical waveguides; and, the first electrode and the second electrode are correspondingly connected to the two electrodes in the functional layer, respectively.

Each of the optical waveguides is of a ridge-shaped optical waveguide structure consisting of a first PDMS lower cladding layer fixed on the PDMS substrate and a first PPSQ core layer located on the first PDMS lower cladding layer.

The Bragg waveguide grating array is formed by connecting more than two Bragg waveguide gratings in series through the optical waveguides; and, each of the Bragg waveguide gratings consists of a second PDMS lower cladding layer fixed on the PDMS substrate, a second PPSQ core layer located on the second PDMS lower cladding layer, and an etching region formed on the second PPSQ core layer.

The PDMS substrate is of a micro-nano porous structure.

The flexible photonic skin provided by the present invention is resistant to electromagnetic interference, small in size, light in weight, good in temperature resistance, high in multiplexing capability and high in sensitivity, and has an equivalent modulus considerable to the modulus of the human skin. The flexible photonic skin is applied to the measurement of vital signs of a human body such as body temperature, pulse, blood pressure, blood glucose and electrocardiogram. The flexible photonic body can realize continuous monitoring of physiological information such as body temperature, pulse, blood pressure, blood glucose and electrocardiogram separately by a Bragg waveguide grating and an MZI electrooptical modulator, thereby improving the portability and comfort of active health monitoring, and can realize the senseless fit with the human body, thereby improving the portability and comfort of active health monitoring.

BRIEF DESCRIPTION OF THE DRAWINGS

The accompanying drawings illustrate one or more embodiments of the present invention and, together with the written description, serve to explain the principles of the invention. Wherever possible, the same reference numbers are used throughout the drawings to refer to the same or like elements of an embodiment.

Figure 1:
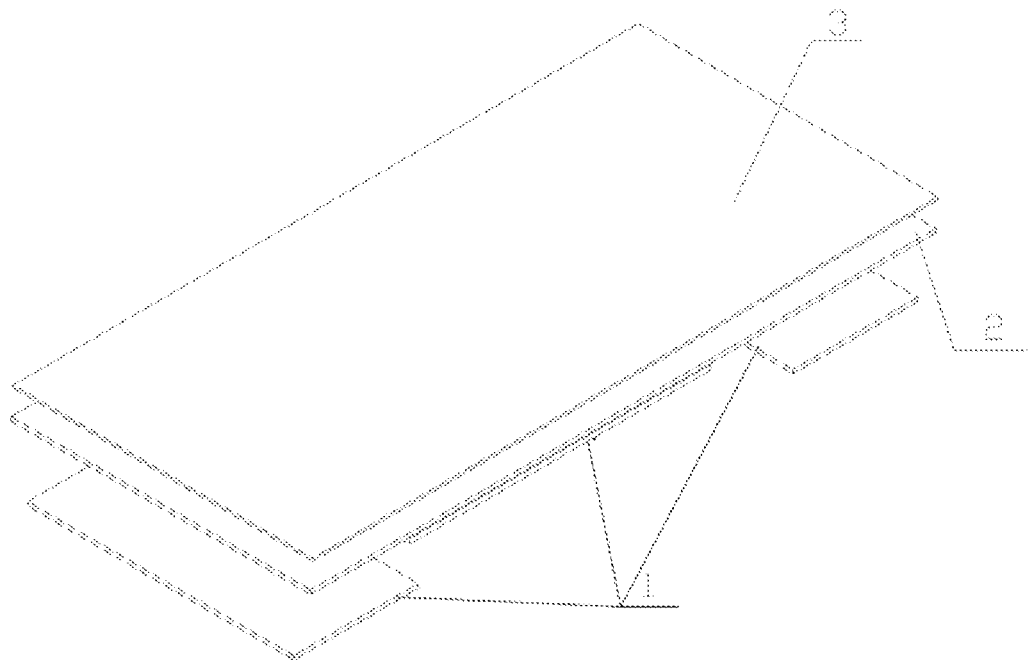
FIG. 1 is a schematic structure diagram of a flexible photonic skin according to the present invention.

in which:

1: functional layer; 2: adhesive layer;

3: packaging layer; 4: electrode;

5: polymer-based photonic integrated chip; 5.1: PDMS substrate;

5.2: Bragg waveguide grating array; 5.21: Bragg waveguide grating;

5.211: second PDMS lower cladding layer; 5.212: second PPSQ core layer;

5.213: etching region; 5.3: optical waveguide;

5.31: first PPSQ core layer; 5.32: first PDMS lower cladding layer;

5.4: input grating coupler array; 5.5: light source;

5.6: first 2×2 coupler; 5.7: arrayed waveguide grating;

5.8: output grating coupler array; 5.9: photodetector array;

5.10: MZI electrooptical modulator; 5.101: first electrode;

5.102: second electrode; 5.103: ground;

5.104: first waveguide arm; 5.105: second waveguide arm;

5.11: first 2×1 coupler; 5.12: second 2×2 coupler;

5.13: second 2×1 coupler.

DETAILED DESCRIPTION OF THE PRESENT INVENTION

The present invention will now be described more fully hereinafter with reference to the accompanying drawings, in which exemplary embodiments of the present invention are shown. The present invention may, however, be embodied in many different forms and should not be construed as limited to the embodiments set forth herein. Rather, these embodiments are provided so that this disclosure is thorough and complete, and will fully convey the scope of the invention to those skilled in the art. Like reference numerals refer to like elements throughout.

Embodiments of the invention are illustrated in detail hereinafter with reference to accompanying drawings. It should be understood that specific embodiments described herein are merely intended to explain the invention, but not intended to limit the invention.

The flexible photonic skin provided by the present invention will be described below in detail by embodiments with reference to the accompanying drawings.

Figure 2:
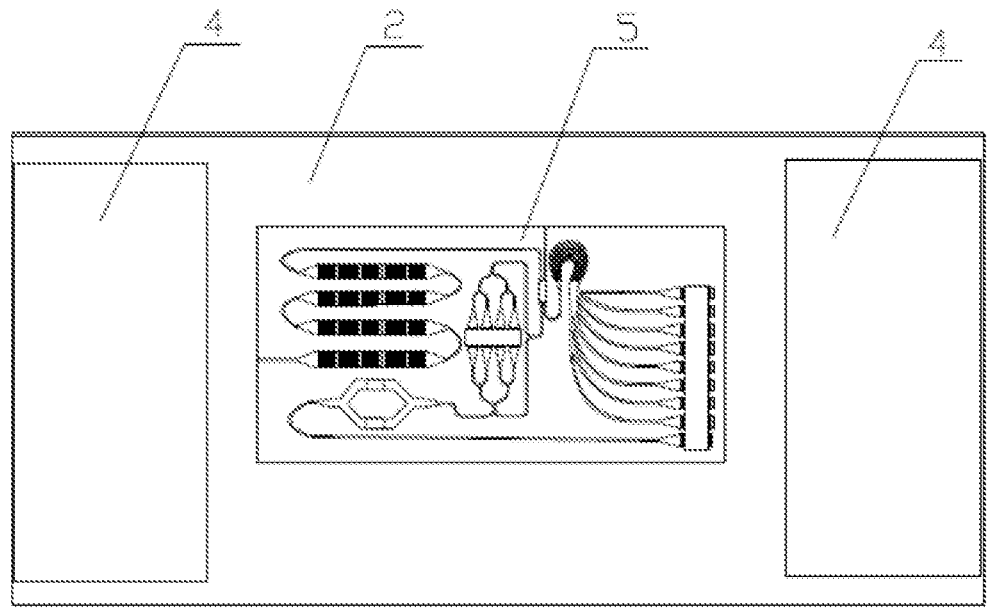
FIG. 2 is a bottom view of FIG. 1.

As shown in FIG. 1 and FIG. 2, the flexible photonic skin provided by the present invention includes a functional layer 1, an adhesive layer 2 used for fixing the functional layer 1 and made of hypoallergenic polyvinyl ethyl ether, and a packaging layer 3 made of a polyurethane semi-transparent film and adhered to the adhesive layer 2, which are arranged successively from the top down, wherein the functional layer 1 consists of two electrodes 4 located on two sides of the flexible photonic skin and used for acquiring electrocardiographic signals of a human body, and a polymer-based photonic integrated chip 5 located between the two electrodes 4 and used for acquiring body temperature, pulse, blood pressure and blood glucose signals of the human body. The polymer-based photonic integrated chip 5 also processes and outputs the acquired electrocardiographic signals of the human body as well as the body temperature, pulse, blood pressure and blood glucose signals of the human body.

Figure 3:
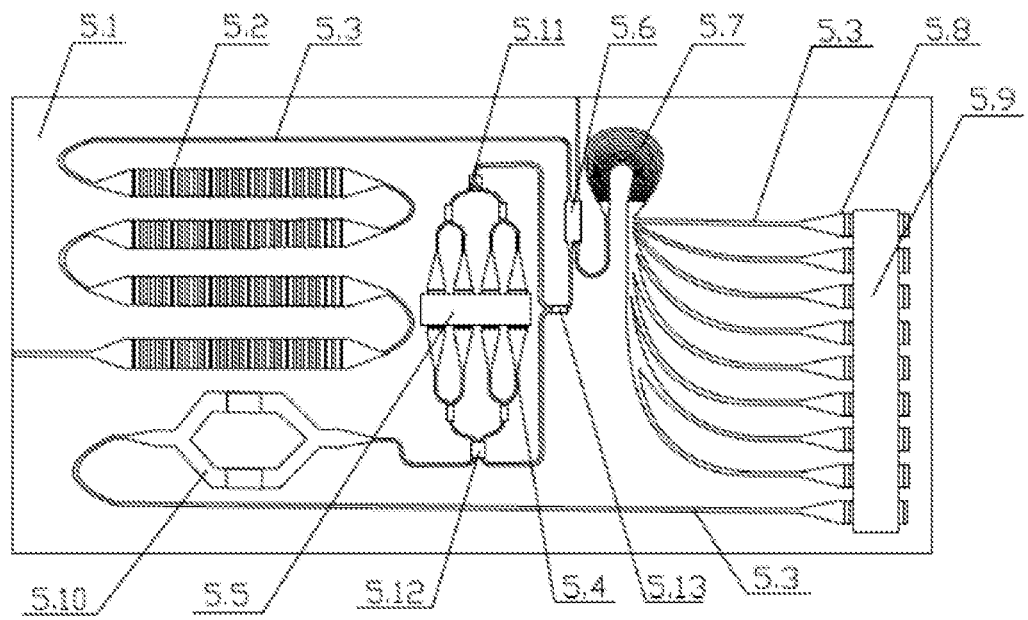
FIG. 3 is a schematic structure diagram of a polymer-based photonic integrated chip according to the present invention.

As shown in FIG. 3, the polymer-based photonic integrated chip 5 includes a PDMS (polydimethylsiloxane) substrate 5.1 which is of a micro-nano porous structure. A Bragg waveguide grating array 5.2, an input grating coupler array 5.4 arranged below a light source 5.5, a MMI coupler 5.6, an arrayed waveguide grating 5.7, an output grating coupler array 5.8 and an MZI electrooptical modulator 5.10, which all are connected through optical waveguides 5.3, are arranged on the PDMS substrate 5.1, respectively. A photodetector array 5.9 is arranged on the output grating coupler array 5.8. A light input and a light output of the Bragg waveguide grating array 5.2 are connected to a first 2×2 coupler 5.6 through the optical waveguides 5.3. The input grating coupler array 5.4 receives output light from the light source 5.5 that is divided into two paths, with one path of light passing through a first 2×1 coupler 5.11 to an input end of a second 2×1 coupler 5.13 through the optical waveguides 5.3, and the other path of light passing through a second 2×2 coupler 5.12 to be separately connected to the MZI electrooptical modulator 5.10 and a light input end of the second 2×1 coupler 5.13 through the optical waveguides 5.3. A light output end of the second 2×1 coupler 5.13 is connected to a light input end of the MMI coupler 5.6, and a light output end of the MMI coupler 5.6 is connected to the Bragg waveguide grating array 5.2 through the optical waveguides 5.3. And, the light output finally coupled by the MMI coupler 5.6 passes through the arrayed waveguide grating 5.7 and the output grating coupler array 5.8 to the photodetector array 5.9 for outputting by means of optical waveguide 5.3.

The input grating coupler array 5.4 consists of four input grating couplers, every two of which are connected in parallel into a group. One end of each input grating coupler is connected to the first 2×1 coupler 5.11 through a 2×1 coupler, while the other end thereof is connected to the second 2×2 coupler through a 2×1 coupler.

The first 2×2 coupler 5.6, the second 2×2 coupler 5.12, the first 2×1 coupler 5.11 and the second 2×1 coupler 5.13 are MMI couplers. The MMI coupler is a kind of integrated waveguide couplers, which main principle is to utilize the self-imaging effect in the light-wave multimode waveguide. When an input light wave propagates in a multimode waveguide, due to the mutually constructive interference of multiple excited modes in the multimode waveguide, a single image or multiple images are reproduced in the propagation direction of the optical field, this phenomenon is called a self-imaging effect. In the embodiments of the present invention, the MMI coupler has a core size of 4 μm×18 μm and 6 μm×100 μm, an additional loss of 0.46 dB, a non-uniformity of 0.06 dB and a wavelength response bandwidth of 100 nm.

The light source 5.5 is bonded to the input grating coupler array 5.4 through BCB (benzocyclobutene) polymer. The photodetector array 5.9 is bonded to the output grating coupler array 5.8 through BCB (benzocyclobutene) polymer.

During the bonding process, the BCB polymer does not simply realize bonding, and the BCB polymer will chemically react at a high temperature to bond two materials through polymerization. The bonding using the BCB polymer includes the following steps: 1: cleaning; 2: drying; 3: spin-coating the BCB polymer; 4: evaporating the solvent; 5: pre-curing and pasting; and, 6: pre-bonding and thermally curing. Firstly, an SOI chip is to be cleaned to prevent the introduction of impurities during the bonding process. During the cleaning process, a chemical reagent is generally used for cleaning. Then, the SOI chip is blow-dried by nitrogen. In order to ensure the dryness of the surface, it is also possible to be dried by heating. Subsequently, the BCB polymer is dispensed by a dispensing machine and then evenly coated by a spin coater. The thickness of the spin coating can be controlled by controlling the spin coater. After a particular spin-coating time, heating is performed to evaporate the solvent, and pre-curing and pasting are then performed. At the end of pasting, pressure is applied to the chip to be bonded from its upper and lower sides to complete a pre-bonding operation, and the sample is continuously heated to a certain temperature for thermally curing.

Figure 4:
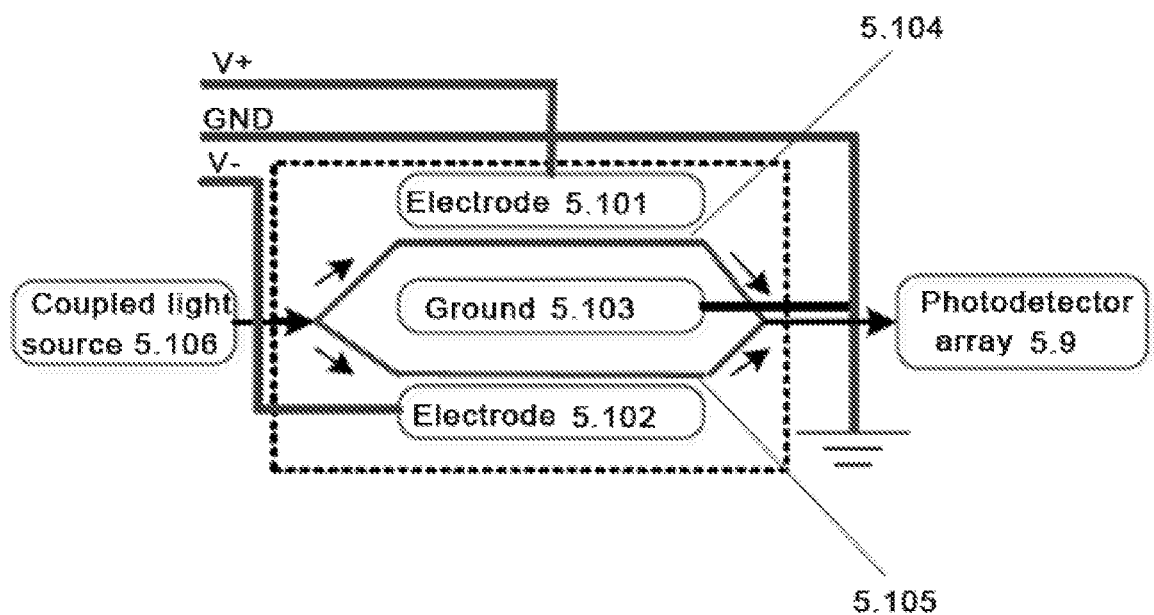
FIG. 4 is a schematic structure diagram of an MZI electrooptical modulator according to the present invention.

As shown in FIG. 4, the MZI electrooptical modulator 5.10 includes a first electrode 5.101, a ground 5.103 and a second electrode 5.102 which are arranged in parallel, wherein a first waveguide arm 5.104 is arranged between the first electrode 5.101 and the ground 5.103, and a second waveguide arm 5.105 is arranged between the ground 5.103 and the second electrode 5.102. Input ends of the first waveguide arm 5.104 and the second waveguide arm 5.105 are connected to a coupled light source 5.106 output from the second 2×2 coupler 5.12 through the optical waveguides 5.3, and output ends of the first waveguide arm 5.104 and the second waveguide arm 5.105 are connected to the input end of the output grating coupler array 5.8 through the optical waveguides 5.3. The first electrode 5.101 and the second electrode 5.102 are correspondingly connected to the two electrodes 4 in the functional layer 1, respectively.

The MZI electrooptical modulator 5.10 mainly uses its electrooptical effect. When the input light wave is divided into two paths of light at a first Y-type branched waveguide on the left side in the flexible photonic skin as shown in FIG. 3, the two paths of light pass through two branched waveguide arms and are applied to an electric field, different phase differences can be generated as the refractivity of the material of the branched waveguide changes with the change in the external fields, and the two paths of light are synthesized into a path of light for outputting by a second Y-type branch on the right.

Figure 5:
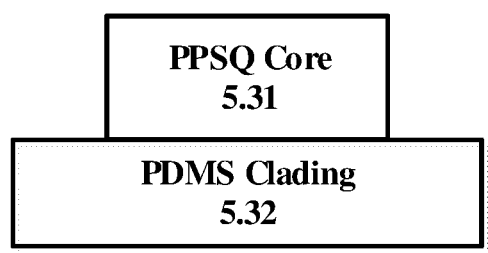
FIG. 5 is a schematic structure diagram of an optical waveguide according to the present invention.

As shown in FIG. 5, each of the optical waveguides 5.3 is of a ridge-shaped optical waveguide structure consisting of a first PDMS lower cladding layer 5.32 fixed on the PDMS substrate 5.1 and a first PPSQ core layer 5.31 located on the first PDMS lower cladding layer 5.32. Outside air forms an upper cladding layer of the optical waveguide 5.3.

The structure of the optical waveguide 5.3 has a strong lateral limiting capability, so a very small bending radius can be realized, and the integration level of the device is thus significantly improved. During the loss analysis on the ridge-shaped optical waveguide structure, the leakage loss and the bending loss are mainly taken into consideration.

The leakage loss $L_{lk}$ (dB/cm) is defined as:

$$L_{lk} = 20 \cdot \log_{10}[\exp(\beta_i)]$$

where $\beta i$ is the imaginary part of the propagation constant. By a finite difference method, the propagation constants $\beta$ of a plurality of PPSQ ridge-shaped optical waveguides under different thicknesses $h_{bf}$ of lower cladding layers are calculated so as to obtain a relationship of change of $L_{lk}$ with $h_{bf}$. By decreasing the width or height of the core layer, the leakage loss of the light wave will be increased. Through calculation and simulation, under the premise of ensuring that the maximum leakage loss of an optical waveguide of a certain size does not exceed 0.1 dB/cm and by considering the uniformity of the PDMS film layer, the optimal $h_{bf}$ is to be selected during the manufacturing process of the device to provide a larger process tolerance.

The bent waveguide is a basic unit of the optical waveguide device. The size of the optical waveguide device is determined by the bending radius to a certain extent. In order to reduce the size of the device and improve the integration level, the most effective method is to reduce the bending radius. However, the reduction of the bending radius will inevitably lead to the increase of the bending loss, influencing the performance of the device. The bending loss generally include two parts, i.e., pure bending loss $L_p$ and transition loss $L_t$, wherein the pure bending loss $L_p$(dB/90°) is derived from the imaginary part $\beta_i$ of the propagation constant of the bent waveguide:

$$L_p = 20\log_{10}[\exp(\pi/2 \cdot R \cdot \beta_i)]$$

where R is the bending radius of the bent waveguide. The transition loss $L_t$ (dB) is caused by the mode mismatch between the straight waveguide and the bent waveguide, and can be calculated from a superposition integral of field distributions of the straight waveguide and the bent waveguide:

$$L_t = -10\log_{10}\left[\frac{\left|\int_{-\infty}^{+\infty}\int_{-\infty}^{+\infty} E_0(x,y)E_0^{B*}(x,y)dxdy\right|^2}{\left|\int_{-\infty}^{+\infty}\int_{-\infty}^{+\infty} E_0(x,y)E_0^{*}(x,y)dxdy\right| \left|\int_{-\infty}^{+\infty}\int_{-\infty}^{+\infty} E_0^{B}(x,y)E_0^{B*}(x,y)dxdy\right|}\right]$$

where * represents the complex conjugation, and $E_0(x, y)$ and $E_0^B(x, y)$ represents the field distributions of the straight waveguide and the bent waveguide, respectively.

In the embodiments of the present invention, the selected ridge-shaped optical waveguide has a width of 6 µm and a height of 220 nm, and the bending radius of the bent waveguide is 55 µm.

As shown in FIG. 3, two ends of the arrayed waveguide grating 5.7 are connected to the optical waveguides 5.3 through Rowland circles, respectively. The arrayed waveguide grating 5.7, having a transmission structure, is an application of the concave grating, which propagates light through a waveguide. The transmission structure enables the arrayed waveguide grating to realize light diffraction in a small size, so that the resolution of grating can be improved and it is easier for the integrated design. Two ends of the waveguide are connected to an input waveguide and an output waveguide, and both the input waveguide and the output waveguide are arranged on Rowland circles. When light is input to the Rowland circle, the Rowland circle will focus and distribute the light and then transmit the light to different arrayed waveguide gratings. At the output end, the Rowland circle refocuses, to the output waveguide, the light transmitted to the arrayed waveguide, so that the function of multiplexing/de-multiplexing the optical wavelength is realized. In the embodiments of the present invention, the arrayed waveguide grating of a conventional structure is used, where the number of input waveguides is 1, the number of output waveguides is 8 and the core size is 300 µm×570 µm.

In the embodiments of the present invention, both the input grating coupler array 5.4 and the output grating coupler array 5.8 are uniform grating couplers. For the input grating coupler, the value of the grating period Λ is 570 nm, the duty ratio is 0.5, the etching depth h is 70 nm, the grating length is 7.98 µm (14 periods), the width is 10 µm, and the coupling efficiency with the light source is 46.5%. For the output grating coupler, the value of the grating period Λ is 700 nm, the duty ratio is 0.7, the etching depth h is 70 nm, the grating length is 25.2 µm (36 periods), the width is 10 µm, and the coupling efficiency with the light source is 30.2%.

Figure 6:
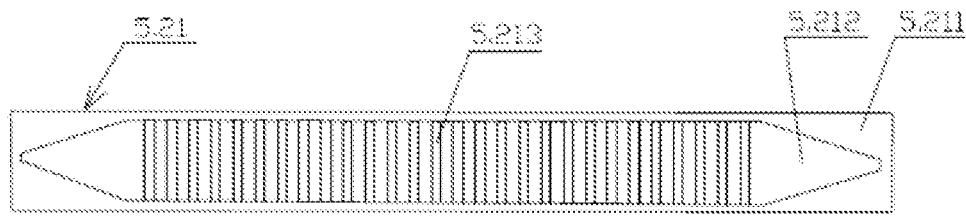
FIG. 6 is a schematic structure diagram of a Bragg waveguide grating according to the present invention.
Figure 7:
FIG. 7 is a lateral view of FIG. 6.

As shown in FIG. 6 and FIG. 7, the Bragg waveguide grating array 5.2 is formed by connecting more than two Bragg waveguide gratings 5.21 in series through the optical waveguides 5.3. Each of the Bragg waveguide gratings 5.21 consists of a second PDMS lower cladding layer 5.211 fixed on the PDMS substrate 5.1, a second PPSQ core layer 5.212 located on the second PDMS lower cladding layer 5.211, and an etching region 5.213 formed on the second PPSQ core layer 5.212.

When the Bragg waveguide gratings 5.21 consists of only the second PDMS lower cladding layer 5.211 and the second PPSQ core layer 5.212, sensing measurement related to the change in the external refractivity is directly performed by the grating formed by the second PPSQ core layer 5.212, so as to realize detection of blood glucose by the Bragg waveguide grating array. By a coupled mode theory, the sensing characteristic of the Bragg waveguide grating array to the change in refractivity of the surrounding medium is analyzed and deduced, and the relationship among the effective refractivity of the surface of the Bragg waveguide grating array, the glucose oxidase layer and the environmental refractivity is measured. By a simple and tractable physical adsorption method, the glucose oxidase is immobilized on the surface of the Bragg waveguide grating array, so that the complicated multi-step chemical modification process required for constructing a biological receptor molecular layer on the surface of the device made of a conventional inorganic material is avoided.

In the flexible photonic skin provided by the present invention, the measurement of skin temperature, pulse and blood pressure and the continuous detection of blood glucose are realized by the Bragg waveguide grating array 5.2. Wherein:

(1) measuring the skin temperature, pulse and blood pressure by the Bragg waveguide grating array: the temperature of the skin is deduced mainly based on the temperature sensitivity of the Bragg waveguide grating array, and the pulse of the human body is deduced based on the pressure sensitivity of the Bragg waveguide grating array, and the blood pressure of the human body is deduced from pulse wave. Therefore, by a mode theory for slab waveguides and an effective refractivity method for rectangular waveguides, the temperature sensitivity and pressure sensitivity of the Bragg waveguide grating array are theoretically analyzed and numerically calculated. Main factors influencing the temperature sensitivity are analyzed: the thermo-optical effects of the material of the first PPSQ core layer 5.212 and the material of the second PDMS lower cladding layer 5.211; and, main factors influencing the pressure sensitivity are analyzed: the elasto-optical effects of the second PPSQ core layer 5.212 and the second PDMS lower cladding layer 5.211, as well as the elastic deformation of the second PPSQ core layer 5.212.

(2) continuous detecting blood glucose by the Bragg waveguide grating array: continuous detecting blood glucose, that is, providing the continuous dynamic change in blood glucose of a diabetic patient in 24 hours, is of great significance for establishing a diabetes treatment scheme and evaluating the therapeutic effect. At present, a minimally invasive blood glucose concentration detection technology is widely used in the medical treatment, where the continuous detection of blood glucose is realize by measuring the concentration of glucose in the tissue fluid. This technology has the characteristics of minimal invasion, higher implementability, fast measurement speed and the like. The minimally invasive blood glucose detection technology is classified into two categories, i.e., measurement by transdermal extraction and measurement by implantation. In the measurement by transdermal extraction, since a small amount of the extracted tissue fluid is to be diluted, the measurement limit of the sensor is required to a very low concentration. In the measurement by implantation, since the measurement accuracy of the sensor will be greatly affected due to factors such as the interference from bioelectricity, the glucose sensor is highly required by the minimally invasive blood glucose detection. In the flexible photonic skin provided by the present invention, the immobilization of enzymes is performed by a physical method, mainly because the physical method is easy to handle and it is also more practical for a wearer to handle the sensor.

Although the principle and implementations of the present invention have been described above by specific examples in the embodiments of the present invention, the foregoing description of the embodiments is merely for helping understanding the method of the present invention and the core concept thereof. Meanwhile, various alterations to the specific implementations and application ranges may come to a person of ordinary skill in the art according to the concept of the present invention. In conclusion, the contents of this specification shall not be regarded as limitations to the present invention.

The foregoing description of the exemplary embodiments of the present invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated.

Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A flexible photonic skin, comprising:
a functional layer;
an adhesive layer configured for fixing the functional layer and made of hypoallergenic polyvinyl ethyl ether; and
a packaging layer made of a polyurethane semi-transparent film and adhered to the adhesive layer, which are arranged successively from the top down;
wherein the functional layer comprises:
two electrodes configured for acquiring electrocardiographic signals of a human body, and
a polymer-based photonic integrated chip located between the two electrodes and configured for acquiring body temperature, pulse, blood pressure and blood glucose signals of the human body;
the polymer-based photonic integrated chip outputs the acquired electrocardiographic signals of the human body as well as the body temperature, pulse, blood pressure and blood glucose signals of the human body; and
the polymer-based photonic integrated chip comprises a PDMS substrate; the PDMS substrate comprises the following which are connected through optical waveguides respectively:
a Bragg waveguide grating array;
an input grating coupler array arranged below a light source;
a Multi-Mode Interference (MMI) coupler;
an arrayed waveguide grating;
an output grating coupler array; and
an MZI electrooptical modulator, wherein
a photodetector array is arranged on the output grating coupler array;
a light input and a light output of the Bragg waveguide grating array are connected to a first 2×2 coupler through optical waveguides;
the input grating coupler array receives output light from the light source that is divided into two paths, with one path of light passing through a first 2×1 coupler to an input end of a second 2×1 coupler through the optical waveguides, and the other path of light passing through a second 2×2 coupler to be separately connected to the MZI electrooptical modulator and a light input end of the second 2×1 coupler through the optical waveguides;
a light output end of the second 2×1 coupler is connected to a light input end of the MMI coupler;
a light output end of the MMI coupler is connected to the Bragg waveguide grating array through the optical waveguides; and
the light output finally coupled by the MMI coupler passes through the arrayed waveguide grating and the output grating coupler array to the photodetector array for outputting by means of optical waveguide.

2. The flexible photonic skin according to claim 1, wherein the first 2×2 coupler, the first 2×1 coupler, the first 2×1 coupler and the second 2×1 coupler are MMI couplers.

3. The flexible photonic skin according to claim 1, wherein the light source is bonded to the input grating coupler array through BCB polymer.

4. The flexible photonic skin according to claim 1, wherein the photodetector array is bonded to the output grating coupler array through BCB polymer.

5. The flexible photonic skin according to claim 1, wherein the MZI electrooptical modulator comprises a first electrode, a ground and a second electrode which are arranged in parallel;
- a first waveguide arm is arranged between the first electrode and the ground,
- a second waveguide arm is arranged between the ground and the second electrode;
- input ends of the first waveguide arm and the second waveguide arm are connected to a coupled light source output from the second 2×2 coupler through the optical waveguides;
- output ends of the first waveguide arm and the second waveguide arm are connected to the input end of the output grating coupler array through the optical waveguides; and,
- the first electrode and the second electrode are correspondingly connected to the two electrodes in the functional layer, respectively.

6. The flexible photonic skin according to claim 1, wherein each of the optical waveguides is of a ridge-shaped optical waveguide structure consisting of a first PDMS lower cladding layer fixed on the PDMS substrate and a first PPSQ core layer located on the first PDMS lower cladding layer.

7. The flexible photonic skin according to claim 1, wherein the Bragg waveguide grating array is formed by connecting more than two Bragg waveguide gratings in series through the optical waveguides; and
- each of the Bragg waveguide gratings consists of a second PDMS lower cladding layer fixed on the PDMS substrate, a second PPSQ core layer located on the second PDMS lower cladding layer, and an etching region formed on the second PPSQ core layer.

8. The flexible photonic skin according to claim 1, wherein the PDMS substrate is of a micro-nano porous structure.

\* \* \* \* \*